US012599436B2

(12) United States Patent
Song et al.

(10) Patent No.: US 12,599,436 B2
(45) Date of Patent: Apr. 14, 2026

(54) METHOD AND APPARATUS FOR TRAINING OPERATION DETERMINATION MODEL FOR MEDICAL INSTRUMENT CONTROL DEVICE

(71) Applicant: Medipixel, Inc., Seoul (KR)

(72) Inventors: Kyo Seok Song, Seoul (KR); Chae Hyeuk Lee, Yongin-si (KR); Kyung Hwan Kim, Seoul (KR)

(73) Assignee: Medipixel, Inc., Seoul (KR)

( * ) Notice: Subject to any disclaimer, the term of this patent is extended or adjusted under 35 U.S.C. 154(b) by 647 days.

(21) Appl. No.: 17/919,407

(22) PCT Filed: Jul. 9, 2021

(86) PCT No.: PCT/KR2021/008799
§ 371 (c)(1),
(2) Date: Jan. 5, 2024

(87) PCT Pub. No.: WO2022/050557
PCT Pub. Date: Mar. 10, 2022

(65) Prior Publication Data
US 2024/0130796 A1    Apr. 25, 2024
US 2024/0225743 A9    Jul. 11, 2024

(30) Foreign Application Priority Data

Sep. 4, 2020    (KR) ......................... 10-2020-0113187

(51) Int. Cl.
A61B 34/20          (2016.01)
A61B 34/10          (2016.01)
A61M 25/09          (2006.01)

(52) U.S. Cl.
CPC .............. *A61B 34/20* (2016.02); *A61B 34/10* (2016.02); *A61M 25/09041* (2013.01);
(Continued)

(58) Field of Classification Search
None
See application file for complete search history.

(56) References Cited

U.S. PATENT DOCUMENTS 10,548,669 B2 *    2/2020    Goyal .................... A61B 34/10
2017/0262733 A1 *    9/2017    Gulsun ................ G06V 10/454
(Continued)

FOREIGN PATENT DOCUMENTS

JP            2019510547 A        4/2019

OTHER PUBLICATIONS

Wu J, Wang H, Zhang P, Ma X, Hu Q. A preliminary real-time and realistic simulation environment for percutaneous coronary intervention. Biomed Res Int. 2015;2015:183157. doi: 10.1155/2015/183157. Epub Mar. 23, 2015. PMID: 25879018; PMCID: PMC4386679. (Year: 2015).*

(Continued)

*Primary Examiner* — David Ometz
(74) *Attorney, Agent, or Firm* — BOND, SCHOENECK & KING, PLLC; George R. McGuire

(57) ABSTRACT

This system for training an operation determination model for a medical instrument control device generates training data by means of a reinforcement learning model, and, using the training data, can train an operation determination model configured to output information associated with operational commands for a driving unit that transports medical instruments.

18 Claims, 12 Drawing Sheets

(52) U.S. Cl.
CPC ... *A61B 2034/104* (2016.02); *A61B 2034/105* (2016.02); *A61B 2034/107* (2016.02); *A61B 2034/2065* (2016.02)

(56) References Cited

U.S. PATENT DOCUMENTS

| | | | | |
|---|---|---|---|---|
| 2019/0125192 A1 | 5/2019 | Kusu et al. | | |
| 2019/0231436 A1* | 8/2019 | Panse | ..................... | A61B 34/30 |
| 2020/0222018 A1* | 7/2020 | van Walsum | ........ | A61B 5/0044 |
| 2021/0057081 A1* | 2/2021 | Mohr | ..................... | G16H 50/50 |
| 2021/0196387 A1* | 7/2021 | Seo | ........................ | A61B 34/25 |
| 2021/0386483 A1* | 12/2021 | Chiou | ....................... | G06T 7/30 |

OTHER PUBLICATIONS

Gherardini M, Mazomenos E, Menciassi A, Stoyanov D. Catheter segmentation in X-ray fluoroscopy using synthetic data and transfer learning with light U-nets. Comput Methods Programs Biomed. Aug. 2020; 192:105420. doi: 10.1016/j.cmpb.2020.105420. Epub Feb. 29, 2020. PMID: 32171151; PMCID: PMC7903142. (Year: 2020).*

"Trajectory Optimization of Robot-Assisted Endovascular Catheterization with Reinforcement Learning" Chi, et al. 2018 IEEE/RSJ International Conference on Intelligent Robots and Systems (IROS) Madrid, Spain, Oct. 1-5, 2018. pp. 1-7.

"GA3C Reinforcement Learning for Surgical Steerable Catheter Path Planning" Segato, et al. 2020 IEEE International Conference on Robotics and Automation (ICRA) May 31-Aug. 31, 2020, Paris France. pp. 1-7.

Non-translated International Search Report and Written Opinion for PCT/KR2021/008799, filed Jul. 9, 2021. pp. 1-6.

* cited by examiner

600a

610a

620a

+78°

+78°

600b

610b

-40°

620b

-40°

900a

900b

900c

1100

METHOD AND APPARATUS FOR TRAINING OPERATION DETERMINATION MODEL FOR MEDICAL INSTRUMENT CONTROL DEVICE

CROSS-REFERENCE TO RELATED APPLICATION(S)

This application is the United States National Phase application filed under 35 U.S.C. 371 of International Application No. PCT/KR2021/008799, filed Jul. 9, 2021, which claims priority to Korean Patent Application No. 10-2020-0113187 filed with the Korean Patent Office on Sep. 4, 2020, the entirety of each of which is hereby incorporated by reference.

TECHNICAL FIELD

The following description relates to a method of training an operation determination model for a medical instrument control device.

BACKGROUND ART

To treat cardiovascular, cerebrovascular, and peripheral blood vessels, an interventional procedure, such as stent insertion, has been widely used. A guidewire is a tool for setting a path of transporting a stent and the like in a blood vessel through a catheter, and a practitioner may transport the guidewire to an endpoint of a diseased blood vessel by using visual information based on a medical image, such as blood vessel angiography, and haptic information based on sense by the hand.

Recently, a technique for alleviating physical burden of a practitioner, such as radiation exposure, and assisting precise control of a surgical tool has been developed. However, a practitioner needs to learn to adapt to a new tool for simple procedure operations.

DISCLOSURE OF THE INVENTION

Technical Solutions

According to an aspect, there is provided a method, performed by a processor, of training an operation determination model of a medical instrument control device, the method includes, when a medical instrument inserted into a vascular model reaches a branching region in the vascular model, identifying a procedure environment in the branching region, selecting a reinforcement learning model corresponding to the identified procedure environment from a plurality of reinforcement learning models and training the selected reinforcement learning model by reinforcement learning based on a vascular patch image extracted for the branching region, after training of the selected reinforcement learning model is finished, calculating a training output based on the selected reinforcement learning model from the vascular patch image for the branching region and generating training data in which the training output pairs with the extracted vascular patch image as a training input, and training the operation determination model by supervised learning based on the generated training data.

The identifying of the procedure environment includes, when the medical instrument reaches the branching region, identifying a branching shape of the branching region based on the vascular patch image extracted for the branching region.

The identifying of the branching shape includes identifying based on an angle difference between a direction of a main branch and a direction of branch closest to a branch point in the vascular patch image.

The identifying of the procedure environment includes, when the medical instrument reaches the branching region, identifying an orientation characteristic of a tip of the medical instrument in the branching region.

The identifying of the orientation characteristic includes, when the medical instrument rotates in a predetermined rotation angle based on a longitudinal direction axis of a medical wire connected to a body of the medical instrument, observing an orientation direction of the tip of the medical instrument, and calculating a ratio of observed directions during rotation of the medical instrument and determining the orientation characteristic based on the calculated ratio.

The identifying of the procedure environment includes, when a plurality of vascular patch images for the branching region is extracted, mapping a procedure environment, which is identified for one vascular patch image from among the plurality of vascular patch images, to the other vascular patch images.

The identifying of the procedure environment includes, until the medical instrument enters the branching region and reaches an outside of the branching region, extracting a plurality of vascular patch images related to the branching region based on a location of the medical instrument that changes each time the medical instrument drives, wherein the training of the selected reinforcement learning model by reinforcement learning includes training the selected reinforcement learning model corresponding to the identified procedure environment, based on the plurality of vascular patch images related to the branching region.

The method further includes preprocessing and simplifying the vascular patch image.

The simplifying includes rotating the vascular patch image such that a proceeding direction of the medical instrument captured in the vascular patch image is oriented to one direction of the vascular patch image and a central axis of a branch where the medical instrument is located is aligned with an axis of the vascular patch image.

The training of the selected reinforcement learning model by reinforcement learning includes, when a reinforcement learning model corresponding to the identified procedure environment for the branching region is not found, excluding at least a portion of vascular patch images related to the branching region from training.

The excluding includes, excluding, from training based on reinforcement learning, vascular patch images related to a branching region having a branching shape with an angle difference that is out of a predetermined angular range designated to a plurality of reinforcement learning models.

The training of the selected reinforcement learning model by reinforcement learning includes iteratively training the plurality of reinforcement learning models by using vascular patch images collected from a plurality of branching regions of one or more vascular models.

The identifying of the procedure environment includes, mapping the identified procedure environment to the vascular patch image, wherein the generating of the training data includes for each of the plurality of vascular patch images collected during training of the plurality of reinforcement learning models, loading a reinforcement learning model corresponding to the procedure environment that is mapped to the vascular patch image, and generating the training output by applying the loaded reinforcement learning model to the vascular patch image.

The training of the operation determination model includes updating a parameter of the operation determination model until a loss between the training output and an output calculated based on the operation determination model from the vascular patch image is less than a threshold loss.

The method further includes, while the medical instrument is inserted, calculating an expectation value for each operation command as an output by using the operation determination model from an input patch image that is extracted based on a location of the medical instrument inserted into a blood vessel without procedure environment information.

The method further includes selecting an operation command having a greatest expectation value among expectation values calculated for each operation command, and performing any one of proceeding, rotating, and retracting of the medical instrument by driving a driving unit connected to the medical instrument based on the selected operation command.

According to another aspect, there is provided a system for training an operation determination model of a medical instrument control device, the system includes a memory configured to store a plurality of reinforcement learning models and operation determination models, and a processor configured to, when a medical instrument inserted into a vascular model reaches a branching region in the vascular model, identify a procedure environment in the branching region, select a reinforcement learning model corresponding to the identified procedure environment among the plurality of reinforcement learning models, train the selected reinforcement learning model by reinforcement learning based on a vascular patch image extracted for the branching region, after training of the selected reinforcement learning model is finished, calculate a training output based on the selected reinforcement learning model from the vascular patch image for the branching region, generate training data in which the training output pairs with the extracted vascular patch image as a training input, and train the operation determination model by supervised learning based on the generated training data.

BEST MODE FOR CARRYING OUT THE INVENTION

Figure 1:
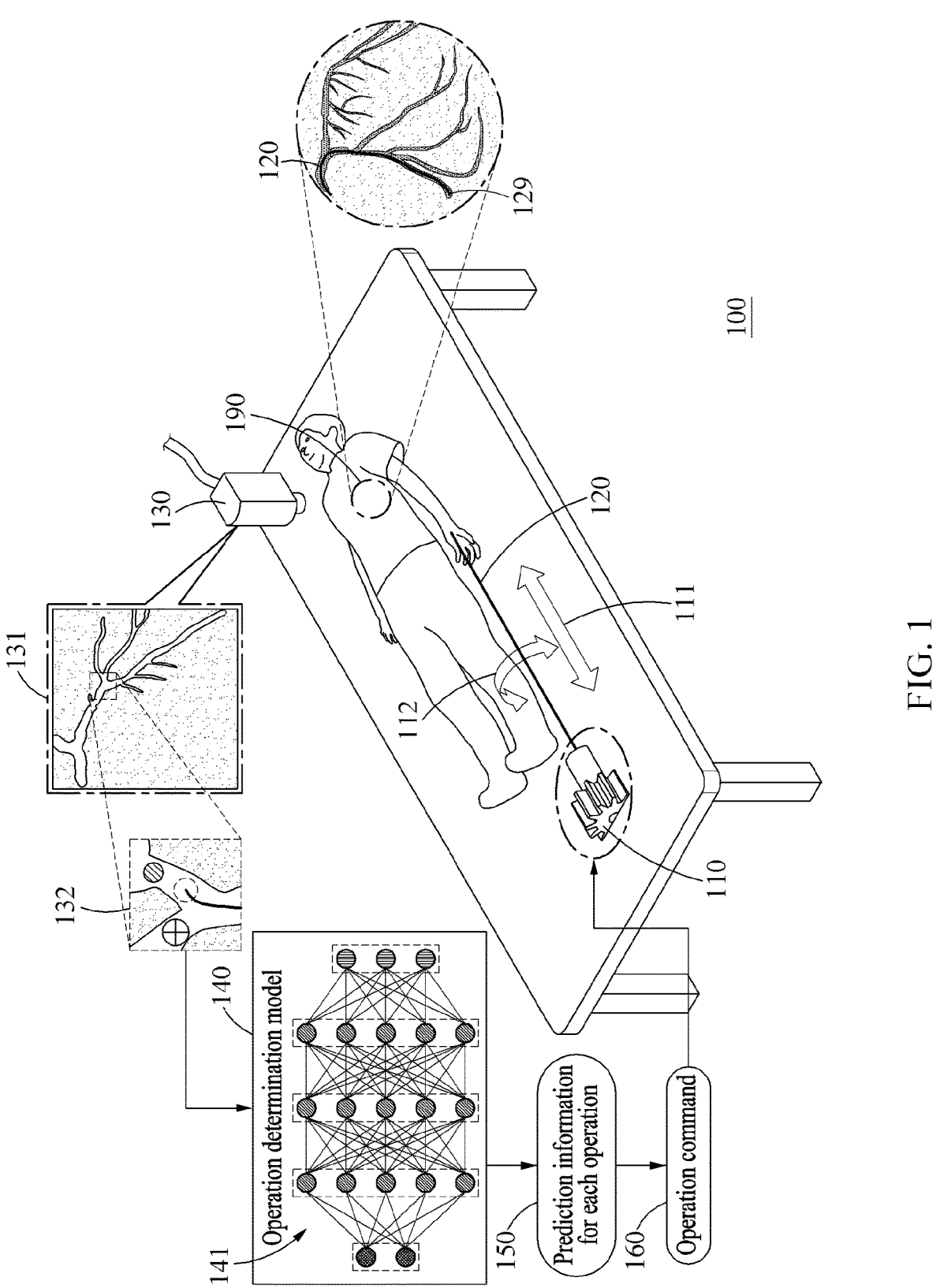
FIG. 1 illustrates a medical instrument control system according to an example embodiment.

Hereinafter, example embodiments will be described in detail with reference to the accompanying drawings. However, various alterations and modifications may be made to the example embodiments. Here, the example embodiments are not construed as limited to the disclosure. The example embodiments should be understood to include all changes, equivalents, and replacements within the idea and the technical scope of the disclosure.

The terminology used herein is for the purpose of describing particular example embodiments only and is not to be limiting of the example embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

Also, in the description of the components, terms such as first, second, A, B, (a), (b) or the like may be used herein when describing components of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

FIG. 1 illustrates a medical instrument control system according to an example embodiment.

A medical instrument control system 100 may be a system for controlling a movement of a medical instrument 129, and the medical instrument control system 100 may include a vascular image capturing device 130 and a medical instrument control device. In FIG. 1, a driving unit 110 of the medical instrument control device is illustrated for ease of description, however, the example is not limited thereto. An example of a configuration of the medical instrument control device is described with reference to FIG. 11.

The vascular image capturing device 130 may be a device for capturing a vascular image 131. The vascular image 131 may represent an image that captures a blood vessel of a target object (e.g., a recipient 190). The vascular image capturing device 130 may capture the vascular image 131 by using coronary angiography (hereinafter, referred to as CAG) or magnetic resonance imaging (hereinafter, referred to as MRI). Not only a blood vessel but the medical instrument 129 may be captured on the vascular image 131. The vascular image 131 may be used as an input to control the medical instrument 129 in a medical instrument control device, which is described below.

The medical instrument control device may transport the medical instrument 129 inserted into a blood vessel to a destination part. Although FIG. 1 illustrates that the medical instrument 129 is inserted into a blood vessel of a wrist of the recipient 190, the example is not limited thereto, and the medical instrument may be inserted into a blood vessel of a nether extremity of the recipient 190. The destination part may be a part where a disease and a lesion potentially or explicitly exist. The medical instrument control device may transport the tip of the medical instrument 129 to the destination part. The medical instrument control device may include a robot configured to transport the medical instrument 129. For example, the medical instrument control device may transport the medical instrument 129 through the driving unit 110.

In the present disclosure, the medical instrument 129 may be a member inserted into a blood vessel and may be a surgical tool that operates based on control by a practitioner (for example, a doctor) and/or a given command. The medical instrument 129 may be, for example, a introducer kit. The medical instrument 129 may be connected to the driving unit 110 through a medical wire 120. The medical wire 120 may be, for example, a catheter or a guidewire. The guidewire may be used for inserting and guiding the medical instrument 129 described above to the destination part of a blood vessel.

The medical instrument control device may control driving of the medical instrument 129 based on a determined operation command 160 while the medical instrument 129 is inserted into the blood vessel. The medical instrument 129 may be connected to the driving unit 110 and in response to the determined operation command 160, the driving unit 110 may perform an action of the medical instrument 129. Here, the action of the medical instrument 129 may include a proceed/retract action 111 and a rotate action 112. The operation command 160 may be a command to operate the driving unit 110 connected to the medical instrument 129 to perform an action of the medical instrument 129, and may include, for example, a command to proceed (hereinafter, referred to as a proceed action) the medical instrument 129, a command to retract the medical instrument 129 (hereinafter, referred to as a retract action), and a command to rotate the medical instrument 129 (hereinafter, a rotate action). For reference, for the rotate action in the present disclosure, it is described that a rotation direction is one direction (for example, clockwise) based on a predetermined reference axis (for example, an axis in a longitudinal direction of the medical wire 120), however, the example is not limited thereto, and the rotation direction may be a clockwise direction and a counterclockwise direction based on each reference direction depending on the design.

The driving unit 110 may include at least one motor and a mechanical power transmission structure configured to convert a rotational force of the motor into a straight-line motion and/or a rotary motion of a desired axis. For example, the driving unit 110 may proceed the medical instrument 129 through driving that pushes the medical instrument 120 in response to the proceed command. For example, the driving unit 110 may retract the medical instrument 129 through driving that pulls the medical instrument 120 in response to the retract command. In response to the rotate command, the driving unit 110 may rotate the medical instrument 129 through driving that rotates the medical instrument 120 based on a longitudinal axis of the medical instrument 120 as a reference axis.

The medical instrument control device may determine the driving command described above by using the vascular image 131. The medical instrument control device may extract an input patch image 132 from the vascular image 131 and may output, from the extracted input patch image 132, information to determine the operation command 160 based on an operation determination model 140. The input patch image 132 may be a patch corresponding to a part in the blood vessel in the vascular image 131 and may be a preprocessed image. An example of preprocessing and the input patch image 132 is described with reference to FIGS. 3 and 6. The medical instrument control device may calculate prediction information for each operation 150 by performing an operation using the operation determination model 140 on the input patch image 132. For example, the medical instrument control device may input a patch image to an input layer of the operation determination model 140, may transmit a value to a subsequent layer, and may output the prediction information for each operation 150 from an output layer.

The operation determination model 140 may be a machine learning model designed and trained to output the prediction information for each operation 150 from the input patch image 132 and may include, for example, a neural network 141. The prediction information for each operation 150 may be a predicted expectation level in which the medical instrument 129 reaches a target area and/or a final destination area (hereinafter, also referred to as the final destination region) when each operation is applied to the medical instrument 129 from the current location (for example, a location at the time point when the input patch image 132 is captured) of the medical instrument 129 in the input patch image 132 and may include an expectation value for each operation. The final destination region may represent a point and/or a region where a medical instrument needs to finally reach in a blood vessel of a recipient, and the target area may represent an intermediate stopover, which is a point and/or a region in a vascular patch image where the medical instrument needs to pass to reach the final destination region. The prediction information for each operation 150 is described below with reference to FIG. 7. The medical instrument control device may determine the operation command 160 based on the prediction information for each operation 150. The medical instrument control device may apply an action corresponding to the operation command 160 to the medical instrument 129 by driving the driving unit 110 in response to the determined operation command 160.

The neural network 141 may be an example of a deep neural network (DNN). The DNN may include a fully connected network (FCN), a deep convolutional network (DCN), and a recurrent neural network (RNN). The neural network may perform various tasks (for example, determining the operation command 160 to transport the medical instrument 129) by mapping input data to output data in a non-linear relationship, based on deep learning. Deep learning may be a machine learning scheme and may map input data and output data to each other through supervised or unsupervised training.

The neural network 141 may include an input layer, a hidden layer, and an output layer. Each of the input layer, the hidden layer, and the output layer may include a plurality of nodes. The hidden layer may include a plurality of layers. In the neural network 141, nodes of layers other than the output layer may be connected to nodes of a subsequent layer through links for transmitting output signals and the links may connect the layers in various structures. To each node included in the hidden layer, an output of an activation function associated with weighted inputs of nodes included in a previous layer may be input. The weights may be referred to as parameters of the neural network 141. The activation function may include sigmoid, hyperbolic tangent (tanh) and rectified linear unit (ReLU), and nonlinearity may be formed in the neural network 141 by the activation function. In one embodiment, when input data is provided to the neural network 141, the neural network 141 may calculate a function value (for example, an expectation value for each operation command) for each class (for example, operation commands) in the output layer through the hidden layer. In addition, for ease of description, the present disclosure describes that when the neural network 141 calculates an expectation value for each operation command, a processor of the medical instrument control device selects the operation command 160 having the greatest expectation value, however, the example is not limited thereto. The operation determination model 140 may be integrally include an operation of calculating an expectation value for each operation command and an operation of selecting an operation command.

When the width and the depth of the neural network 141 are sufficiently great, the neural network 141 may have a capacity sufficient to implement a predetermined function. When the neural network 141 learns a sufficient quantity of training data through an appropriate training process, the neural network 141 may achieve an optimal inference performance.

Although FIG. 1 describes the neural network 141 for the operation determination model 140, the example is not limited thereto, and a reinforcement learning model may be implemented by the neural network 141. The operation determination model 140 and the reinforcement learning model may each include the neural network 141 having the same or a similar capacity (for example, depth). The operation determination model 140 and the reinforcement learning model may have the neural network 141 having the same structure (for example, a U-net structure), however, the example is not limited thereto.

The medical instrument control system 100 according to an example embodiment may enable an interventional procedure, such as inserting a stent by using a catheter, to treat a disease, such as a cardiovascular disease, a cerebrovascular disease, and a bile duct disease, while a practitioner is spaced apart from an image capturing device using radiation. The medical instrument control system 100 may use the operation determination model 140 flexibly operable in various procedure environments.

Training data may need to be collected for training the operation determination model 140. However, since training data may not be collected using a real living body, a human model phantom may be used. The human model phantom may be a model that mimics human organs, and for example, a tissue equivalent phantom may be a model including a material that may most similarly represent a characteristic of human tissue. In the present disclosure, a vascular model may be a model manufactured by mimicking a blood vessel of at least a portion of tissue or an organ of a human body. In the present disclosure, the vascular model is mainly described as a model including a physical material, however, the example is not limited thereto, and the vascular model may be a simulator model in which a vascular structure of a human body is virtually implemented. Hereinafter, a process of training a reinforcement learning model and the operation determination model 140 by performing an experiment or a simulation until a medical instrument reaches a destination region by inserting the medical instrument into the vascular model is described.

Figure 2:
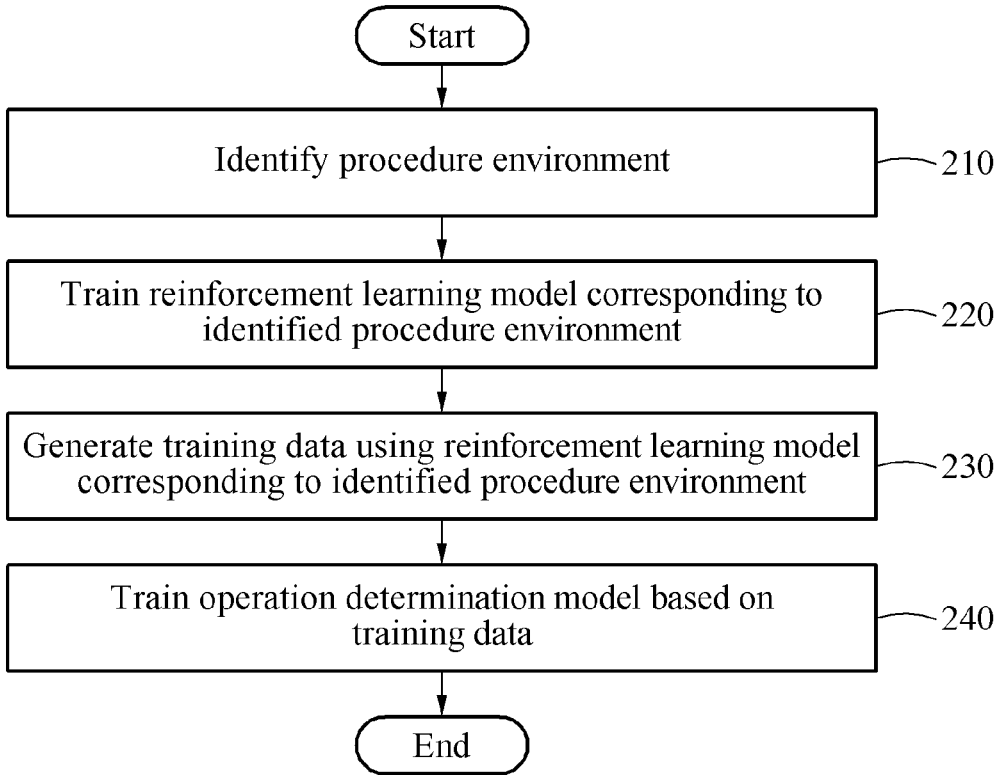
FIG. 2 is a flowchart illustrating a method of training an operation determination model of a medical instrument control device, according to an example embodiment.

FIG. 2 is a flowchart illustrating a method of training an operation determination model of a medical instrument control device according to an example embodiment.

A training apparatus according to one embodiment may primarily train a reinforcement learning model using reinforcement learning for a vascular model, may generate training data based on a result of reinforcement learning, and may secondarily train an operation determination model using the training data.

In operation 210, the training apparatus may identify a procedure environment. When a medical instrument inserted into a vascular model reaches a branching region in the vascular model, the training apparatus may identify a procedure environment in the branching region. The branching region may be a region where a blood vessel branches off and may represent a region defined based on a branch point where branches of blood vessels intersect with each other. The branching region is described with reference to FIG. 4. The procedure environment may be an environment that a medical instrument encounters and relates to movement of the medical instrument, and may include, for example, an orientation characteristic of the medical instrument and a branching shape of a branch included in the branching region where the medical instrument reaches. The orientation characteristic is described with reference to FIG. 5, and the branching shape is described with reference to FIGS. 6A and 6B.

Related to reinforcement learning, which is described below, a compensation value for each action may be calculated through a physical and/or virtual interaction for the vascular model and/or a simulator. In addition, the training apparatus may manage a plurality of reinforcement learning models, which are independent and distinguishable from each other by a procedure environment. Thus, when a medical instrument encounters a branch point during exploration in which the training apparatus moves the medical instrument, the training apparatus may need to select a reinforcement learning model for training from the plurality of reinforcement learning models. The training apparatus may identify a procedure environment corresponding to the branch point to select the reinforcement learning model.

In operation 220, the training apparatus may train the reinforcement learning model corresponding to the identified procedure environment. The training apparatus may select the reinforcement learning model corresponding to the identified procedure environment from the plurality of reinforcement learning models and may train the selected reinforcement learning model by reinforcement learning based on a vascular patch image extracted with respect to the branching region.

In operation 230, the training apparatus may generate training data by using the reinforcement learning model corresponding to the identified procedure environment. After training of the selected reinforcement learning model is finished, the training apparatus may calculate a training output from the vascular patch image on the branching region based on the selected reinforcement learning model and may generate training data paring the training output with the extracted vascular patch image as a training input. The training data may be data including a pair of a training input and a training output, and the training output may represent a ground truth for the training input. The training apparatus may calculate the training output for vascular patch images that are collected for reinforcement learning by using the reinforcement learning model corresponding to the procedure environment of each vascular patch image. In other words, during reinforcement learning exploration of the vascular model, the training apparatus may generate training data according to the number of vascular patch images collected for training the reinforcement learning model.

A required action may vary depending on a location of a medical instrument for each procedure environment of a blood vessel, and the training apparatus may generate training data by using trained reinforcement learning models optimized for each procedure environment. Thus, the training apparatus may efficiently and accurately collect training data that indicates information (for example, an expectation value for each operation) to derive an optimal action at each location among various locations of the medical instrument in various procedure environments in various vascular models.

In operation 240, the training apparatus may train the operation determination model based on the training data. The training apparatus may train the operation determination model by supervised learning based on the generated training data.

Figure 3:
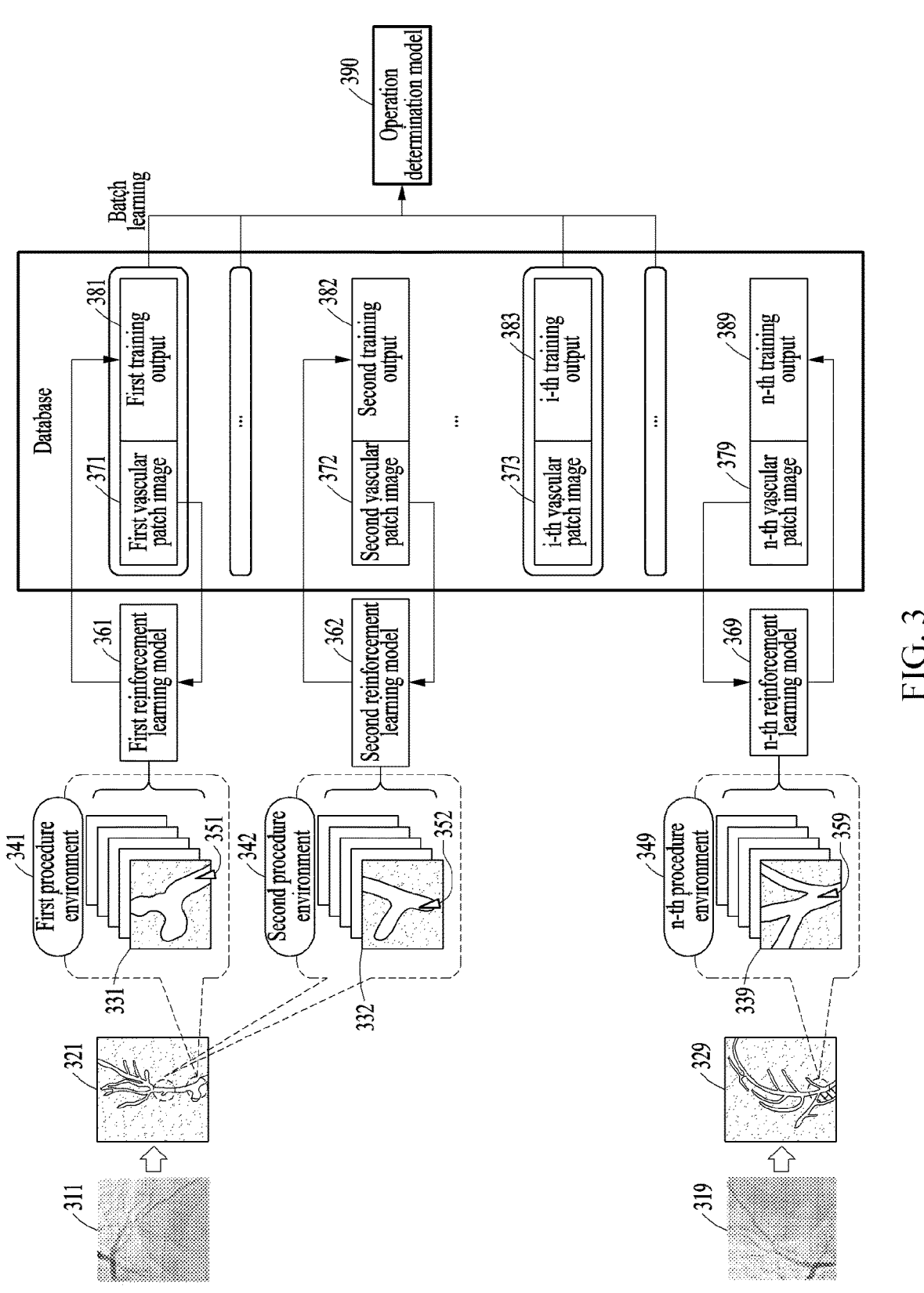
FIG. 3 illustrates an overall operation of generating training data for an operation determination model according to an example embodiment.

FIG. 3 illustrates an overall operation of generating training data for an operation determination model according to an example embodiment.

The training apparatus may perform reinforcement learning and capture a vascular image 311 while moving a medical instrument for a vascular model. For example, the training apparatus and/or a vascular image capturing device may generate an image 321 (hereinafter, referred to as a preprocessed image) obtained by preprocessing the vascular image 311. The preprocessed image 321 may be an image that segments a region corresponding to a blood vessel in the angiographic image. The training apparatus may extract vascular patch images from the preprocessed image 321 based on a location of the medical instrument.

When a medical instrument 351 reaches a first branching region in the vascular model, the training apparatus may identify a first procedure environment corresponding to the first branching region. The training apparatus may map a first procedure environment 341 to a plurality of first vascular patch images 331 extracted for the first branching region. The training apparatus may train a first reinforcement learning model 361 by using the plurality of first vascular patch images 331 to which the first procedure environment 341 is mapped.

In addition, when a medical instrument 352 reaches a second branching region in the vascular model, the training apparatus may identify a second procedure environment corresponding to the second branching region. The training apparatus may map a second procedure environment 342 to a plurality of second vascular patch images 332 extracted for the second branching region. The training apparatus may train a second reinforcement learning model 362 by using the plurality of second vascular patch images 332 to which the second procedure environment 342 is mapped.

The training apparatus may perform reinforcement learning and capture another vascular image 319 while moving a medical instrument for another vascular model. For example, the training apparatus and/or the vascular image capturing device may generate an image 329 (hereinafter, referred to as a preprocessed image) obtained by preprocessing the other vascular image 319. Similar to the above description, when a medical instrument 359 reaches an n-th branching region in a vascular model, the training apparatus may identify an n-th procedure environment corresponding to the n-th branching region. In this example, n may be an integer greater than or equal to 2. The training apparatus may map an n-th procedure environment 349 to a plurality of n-th vascular patch images 339 extracted for the n-th branching region. The training apparatus may train an n-th reinforcement learning model 369 by using the plurality of n-th vascular patch images 339 to which the n-th procedure environment 349 is mapped.

As illustrated in FIG. 3, the procedure environment may be divided by a branching shape and an orientation characteristic of a medical instrument regardless of sameness of the vascular model. In other words, different procedure environments may be identified for each branch in the same vascular model and the same procedure environments may be identified in different vascular models. Thus, when a medical instrument having a predetermined orientation characteristic passes three types of branching shapes during an experiment for one vascular model, the training apparatus may experience three environments.

When training of a plurality of reinforcement learning models for various procedure environments (for example, various branches in various vascular models and a plurality of attempts in the same vascular model) is finished, the training apparatus may generate training data.

As described above, the training apparatus may map the identified procedure environment for each vascular patch image to the vascular patch image. After training of the plurality of reinforcement learning models is finished, for each of the plurality of vascular patch images collected during training of the plurality of reinforcement learning models, the training apparatus may load a reinforcement learning model corresponding to the procedure environment mapped to the vascular patch image. The training apparatus may generate a training output by applying the loaded reinforcement learning model to the vascular patch image. The training output may include expectation values that are predicted when an action based on each operation command is applied to the medical instrument at a predetermined location. As described above, the expected value for each operation command may be a value indicating a predicted expectation level of reaching a target area (for example, an intermediate stopover in a path to a final destination region) in the vascular image patch and/or a final destination region in a blood vessel of a recipient. For example, the training data may be a pair of {a training input, a training output} and may be {(a training input), (a training output)}={(a vascular patch image), (a first expectation value for a proceed command, a second expectation value for a retract command, a third expectation value for a rotate command)}. For reference, the identified procedure environment described above may be used to generate the training data, however, the identified procedure may not be used to train an operation determination model 390.

For example, the training apparatus may calculate a first training output 381 based on the first reinforcement learning model 361 from a patch image 371 of the first vascular patch images 331. The first training output 381 may include expectation values for each operation estimated by the first reinforcement learning model 361 for the patch image 371. The training apparatus may calculate a second training output 382 based on the second reinforcement learning model 362 from a patch image 372 of the second vascular patch images 332. The second training output 382 may include expectation values for each operation estimated by the second reinforcement learning model 362 for the patch image 372. The training apparatus may calculate an i-th training output 383 based on an i-th reinforcement learning model from a patch image 373 of i-th vascular patch images. In this example, i denotes an integer greater than or equal to 1 and less than or equal to n. The training apparatus may calculate an n-th training output 389 based on an n-th reinforcement learning model 369 from a patch image 379 of n-th vascular patch images.

As described above, the training apparatus may iteratively update a parameter of the operation determination model 390 until a loss between the training output and an output calculated based on the operation determination model 390 from the vascular patch image is less than a threshold loss. For example, the training apparatus may train the operation determination model 390 by extracting training data (for example, the first vascular patch image and the i-th vascular patch image of FIG. 3) of different procedure environments as a batch. However, the example is not limited thereto, and regardless of the procedure environment, the training apparatus may train the operation determination model 390 by randomly extracting batch data from training data collected during and after the reinforcement learning described above.

For reference, as the number of procedure environments increases, the procedure environment may be identified in detail. However, for example, when n=8 and there are 8 procedure environments, not only for the learned procedure environment but also an unlearned procedure environment, the operation determination model 390 configured to output an accurate expectation value for each operation may be provided. Accordingly, the training apparatus may generate and use training data that enables efficient training while providing a more accurate inference performance. Specifically, the operation determination model 390 trained based on the generated training data described above may universally provide an accurate operation control performance for various procedure environments. A medical instrument may pass a non-branching section by assigning a proceed action unless the non-branching section is not a clogged blood vessel. Accordingly, the reinforcement learning model may learn only a branching region that requires sophisticated control.

Figure 4:
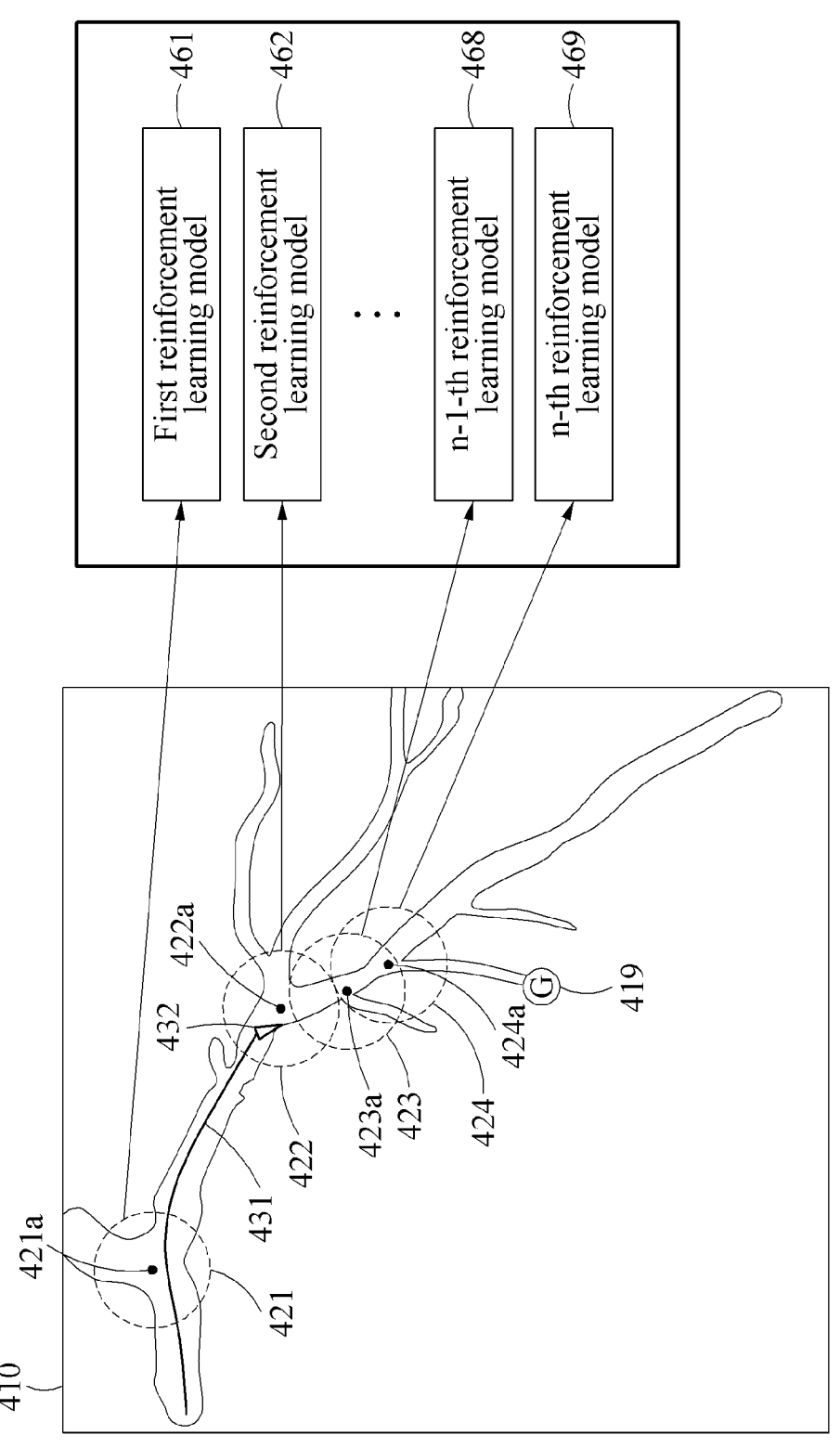
FIG. 4 is a diagram illustrating an example of selecting a plurality of reinforcement learning models by treatment environment according to an example embodiment.

FIG. 4 is a diagram illustrating an example of selecting a plurality of reinforcement learning models by treatment environment according to an example embodiment.

The training apparatus may proceed a medical instrument and may identify a procedure environment of a branching region whenever the medical instrument reaches the branching region. For example, a vascular image 410 of FIG. 4 may include four branching regions 421, 422, 423, and 424 until a destination region 419. Each branching region may be defined based on a branch point where a blood vessel branches off. For example, the training apparatus may set a branching region having a predetermined radius based on a branch point. The first branching region 421 may be set based on a first branch point 421a, the second branching region 422 may be set based on a second branch point 422a, the third branching region 423 may be set based on a third branch point 423a, and the fourth branching region 424 may be set based on a fourth branch point 424a.

In the branching region, an outer point on the upper branch may be a branching start point and an outer point on the lower branch through which a medical instrument passes may be a branching end point. The outer point of the lower branch through which the medical instrument passes may be the target area described above. Determining the lower branch through which the medical instrument passes in each vascular patch image is described with reference to FIG. 10.

After a medical instrument enters a branching region, the training apparatus may extract a plurality of vascular patch images related to the branching region based on a location of the medical instrument that changes for every driving of the medical instrument, until the medical instrument reaches the outside of the branching region. In this case, when the plurality of vascular patch images for the branching region is extracted, the training apparatus may map a procedure environment, which is identified for one vascular patch image from among the plurality of vascular patch images, to the other remaining vascular patch images. For example, the training apparatus may identify a procedure environment for a vascular patch image that is extracted based on a branching start point of a branch and may map the identified procedure environment to other vascular patch images that are extracted up to a branching end point of the branch. The training apparatus may train a selected reinforcement learning model corresponding to the identified procedure environment, based on the plurality of vascular patch images related to the branching region.

For example, the training apparatus may train a first reinforcement learning model 461 by using vascular patch images which are extracted for the first branching region 421, may train a second reinforcement learning model 462 by using vascular patch images which are extracted for the second branching region 422, may train an n−1-th reinforcement learning model 468 by using vascular patch images which are extracted for the third branching region, and may train an n-th reinforcement learning model 469 by using vascular patch images which are extracted for the fourth branching region. In this example, n may be an integer greater than or equal to 2. However, this is only an example, and the example may vary depending on a design and an individual experimental environment.

Figure 5:
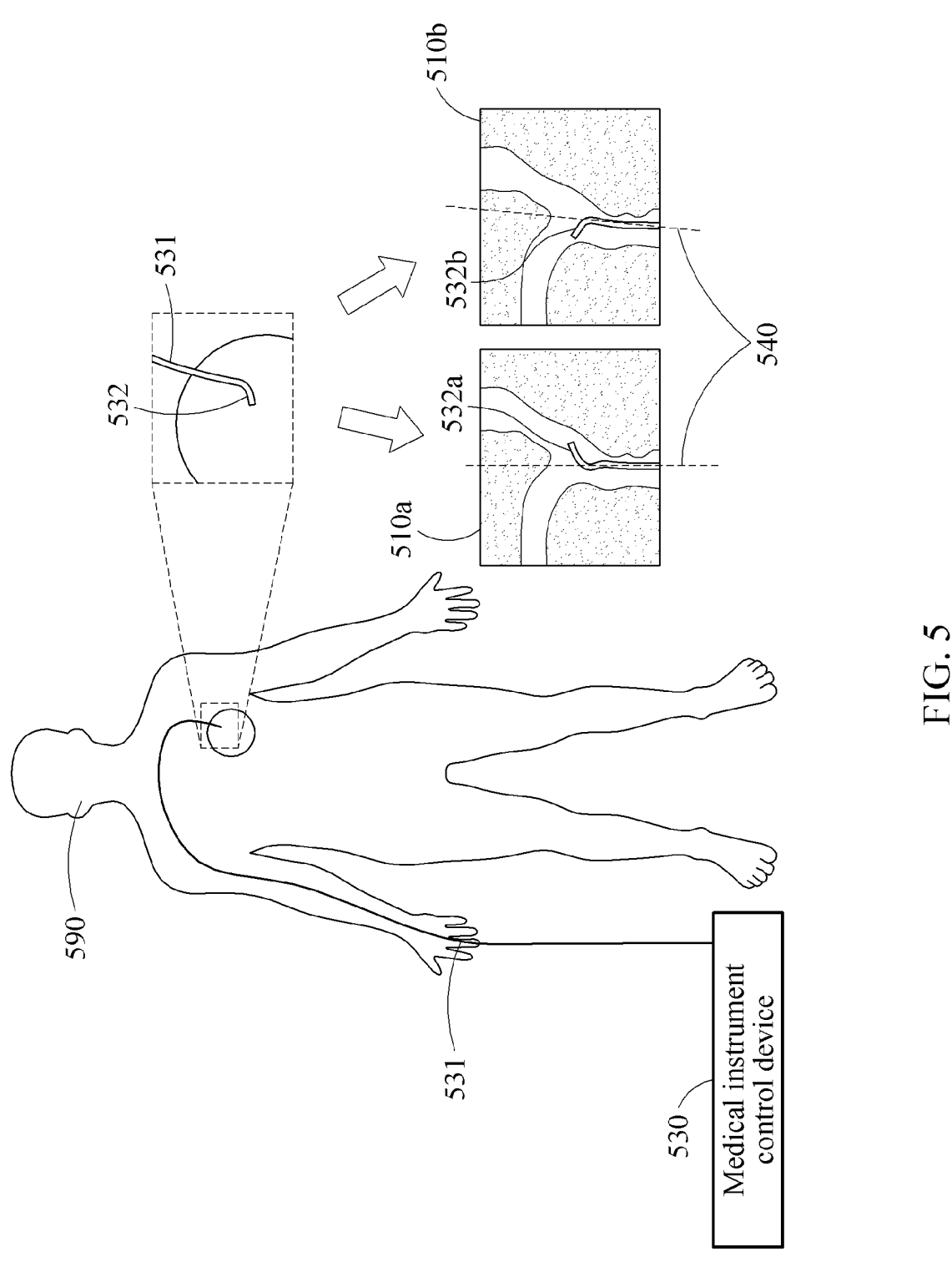
FIG. 5 is a diagram illustrating an orientation characteristic of a medical instrument in a treatment environment according to an example embodiment.

FIG. 5 is a diagram illustrating an orientation characteristic of a medical instrument in a treatment environment according to an example embodiment.

According to an embodiment, a tip 532 of a medical instrument may be connected in antiparallel to a part of a medical wire 531 adjacent to the medical instrument. For example, a longitudinal axis of the tip 532 of the medical instrument may intersect with a longitudinal axis of the part of the medical wire 531 adjacent to the medical instrument. In other words, the tip 532 of the medical instrument may be obliquely connected to the medical wire 531. A catheter and a guidewire may be used as the medical wire 531 connected to the medical instrument for cardiovascular, cerebrovascular, and bile duct interventions, and most of the medical wire 531 may include an elastic material, for example, a flexible wire. The tip 532 of the medical instrument may be slightly bent or twisted such that the medical instrument and the medical wire 531 may be easily oriented to a destination branch while proceeding in the blood vessel. For example, when a medical instrument control device 530 rotates the medical instrument based on the longitudinal direction axis of the medical wire 531 and the tip 532 of the medical instrument faces the right in an image, the medical instrument may easily enter the right branch in the image. Conversely, when the tip 532 faces the left in the image, the medical instrument may easily enter the left branch.

The practitioner may find it difficult to rotate the tip 532 of the medical instrument in a desired direction. For example, in the case of cardiovascular intervention, a medical instrument may not be directly inserted into the cardiovascular system and may be inserted into the cardiovascular system by passing through the artery of a human 590 from the wrist or the groin. In this case, as illustrated in FIG. 5, the shape of the medical wire 531 may not be maintained in a straight line and may bend in the shape of the artery. To rotate the tip 532 of the medical instrument, the medical wire 531 may need to rotate, however, the tip 532 of the medical instrument may not smoothly rotate because of an error in transmission of a rotational force due to a frictional force generated by contact between the artery and the bent shape of the medical wire 531. Due to the reason described above, while the medical instrument is inserted into a vascular model or a blood vessel of a human body, the tip 532 may tend to be oriented in one direction. This may be similar to a case where a wire rolled into a circle does not easily rotate in an axis direction of the wire. In the present disclosure, the tendency in which the tip 532 of the medical instrument tends to be oriented in one direction may be an orientation characteristic of the medical instrument.

Depending on an orientation characteristic of a medical instrument, a strategy required for medical instrument control may vary. For example, for a branching region in the same branching shape, a medical instrument control method may be different for a case where the medical instrument having a left orientation characteristic enters the branching region and a case where the medical instrument having a right orientation characteristic enters the branching region. Since the tip 532 may temporarily face a direction opposite to the orientation characteristic, the orientation characteristic may not be identified by a single frame image, and thus, a description of identifying the orientation characteristic is provided below.

When a medical instrument reaches a branching region, the training apparatus may identify an orientation characteristic of the tip 532 of the medical instrument in the branching region. The tip 532 may be a curved tip. For example, when the medical instrument rotates in a predetermined rotation angle based on a longitudinal direction axis of the medical wire 531 connected to the body of the medical instrument, the training apparatus may observe an orientation direction of the tip 532 of the medical instrument. For example, the training apparatus may rotate the medical instrument by 30° in one step, for a total of 720°. The training apparatus may rotate the medical instrument through 24 steps and may capture the orientation direction of the tip 532 of the medical instrument for each of 24 steps. The training apparatus may record the orientation direction of the tip 532 of the medical instrument for each step. The training apparatus may only record the left or right direction in each step without information on the degree of bending.

For example, in a patch image (hereinafter, referred to as a step image) captured for each step, the training apparatus may identify a first side and a second side, which is opposite to the first side, based on a longitudinal direction axis 540 of the medical wire 531 adjacent to the medical instrument. The training apparatus may record a first side direction when the tip of the medical instrument is oriented to the first side and a second side direction when the tip of the medical instrument is oriented to the second side. In a first step image 510a, since a tip 532a is oriented to the first side (for example, the left side), the training apparatus may record the left direction and in a second step image 510b, since a tip 532b is oriented to the second side (for example, the right side), the training apparatus may record the right direction. For reference, an axis (for example, a vertical axis) of a patch image herein may be aligned with a proceeding direction of the medical instrument.

The training apparatus may calculate a ratio of observed directions during rotation of the medical instrument and may identify the orientation characteristic based on the calculated ratio. For example, the training apparatus may determine the orientation characteristic of the medical instrument based on a ratio of step images in which the first side direction is recorded to the total step images. For example, the training apparatus may determine the orientation characteristic of the medical instrument based on Table 1 shown below. In Table 1, L may denote a left-bending characteristic, R may denote a right-bending characteristic, and N may denote a neutral characteristic.

TABLE 1

| Ratio of left direction of 24 steps | Orientation characteristic of medical instrument |
| --- | --- |
| 0~40% | R (Right-oriented) |
| 41~60% | N (Neutral-oriented) |
| 61~100% | L (Left-oriented) |

According to Table 1 above, when 0% to 40% of 24 step images are recorded as the left direction, the training apparatus may identify that an orientation characteristic of the medical instrument in the branching region is the right orientation characteristic. When 41% to 60% of images are recorded as the left direction, the training apparatus may identify that the orientation characteristic of the medical instrument in the branching region is the neutral orientation characteristic. When 61% to 100% of images are recorded as the left direction, the training apparatus may identify that the orientation characteristic of the medical instrument in the branching region is the left orientation characteristic.

Figure 6A:
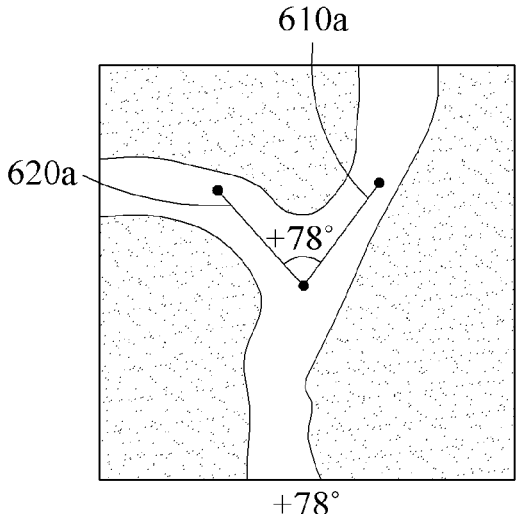
FIGS. 6A and 6B are diagrams illustrating a branching shape as a treatment environment according to an example embodiment.
Figure 6B:
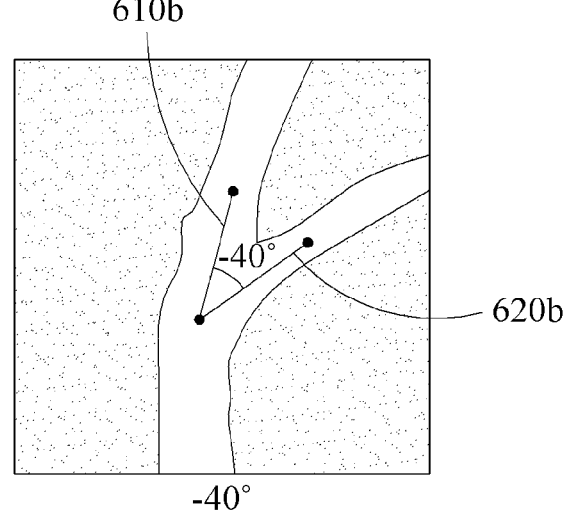

FIGS. 6A and 6B are diagrams illustrating a branching shape as a treatment environment according to an example embodiment.

When a medical instrument reaches a branching region, the training apparatus may identify a branching shape of the branching region based on a vascular patch image extracted for the branching region. For example, the training apparatus may identify the branching shape based on an angle difference between a direction of a main branch and a direction of branch (for example, a side branch) closest to a branch point in the vascular patch image. Thus, when three or more branches appear on an upper branch where the medical instrument is located in one vascular patch image, only the branch corresponding to the main branch and the branch closest to the branch point among the three or more branches may be considered for branching shape determination.

For example, the training apparatus may classify the shape of a blood vessel based on the degree and the direction where the adjacent branch is widened based on the main branch. Like a patch 600a of FIG. 6A, +78 degrees may represent a case where a direction 620a of the adjacent branch forms an angle of 78 degrees on the left side based on a direction 610a of the main branch. Like a patch 600b of FIG. 6B, −40 degrees may represent a case where a direction 620b of the adjacent branch forms an angle of 40 degrees on the right side based on a direction 610b of the main branch.

As described above, a procedure environment may be classified based on the orientation characteristic of the medical instrument described with reference to FIG. 5 and the branching shape described with reference to FIGS. 6A and 6B. For example, the procedure environment may be defined by a pair of (an orientation characteristic, a branching shape). (L, +36 degrees) may represent an environment in which a branch vessel forms 36 degrees on the left side with a left-bending orientation characteristic. (L, −27 degrees) may represent an environment in which a branch vessel forms 27 degrees on the right side with a left-bending orientation characteristic. (R, −27 degrees) may represent an environment in which a branch vessel forms 27 degrees on the right side with a right-bending orientation characteristic. (N, +60 degrees) may represent an environment in which a branch vessel forms 60 degrees on the left side with a neutral orientation characteristic.

As described above, the training apparatus may select a reinforcement learning model to be trained by using a vascular patch image based on an identified procedure environment for the vascular patch image. An angular range and an orientation characteristic may be assigned to each reinforcement learning model, and the training apparatus may select a reinforcement learning model in which an angular range and an orientation characteristic, which correspond to an identified procedure environment for a branching region where the medical instrument enters, are assigned. The environments assigned to the plurality of reinforcement learning models may be classified as Table 2 shown below.

TABLE 2

| Environment | Orientation characteristic | Branching shape |
|---|---|---|
| Environment 1 | L | −90~−70° |
| Environment 2 | L | −50~−30° |
| Environment 3 | L | +30~+50° |
| Environment 4 | L | +70~+90° |
| Environment 5 | R | −90~−70° |
| Environment 6 | R | −50~−30° |
| Environment 7 | R | +30~+50° |
| Environment 8 | R | +70~+90° |

In Table 2, 8 types of environments are defined and reinforcement learning models for each of the environments may be independently prepared and trained. In other words, the training apparatus may select and train one reinforcement learning model from 8 reinforcement learning models. An operation determination model trained by using training data that reinforcement-learned by dividing into 8 types of environments may show more than 90% of the success probability in a simulator and a phantom environment experiment. In Table 2, the angular range for each environment corresponding to each reinforcement learning model may have a range of 20 degrees.

When a reinforcement learning model corresponding to an identified procedure environment for a branching region is not found, the training apparatus according to an example embodiment may exclude vascular patch images associated with the branching region from training. For example, the training apparatus may exclude, from training based on reinforcement learning, vascular patch images associated with a branching region having a branching shape with an angle difference that is out of a predetermined angular range designated to a plurality of reinforcement learning models. Referring to Table 2, a procedure environment of (L, −60 degrees) does not belong to any environment, and thus, the training apparatus may discard a patch image of the environment. In addition, the training apparatus may partially discard vascular patch images having a neutral orientation characteristic.

Figure 7:
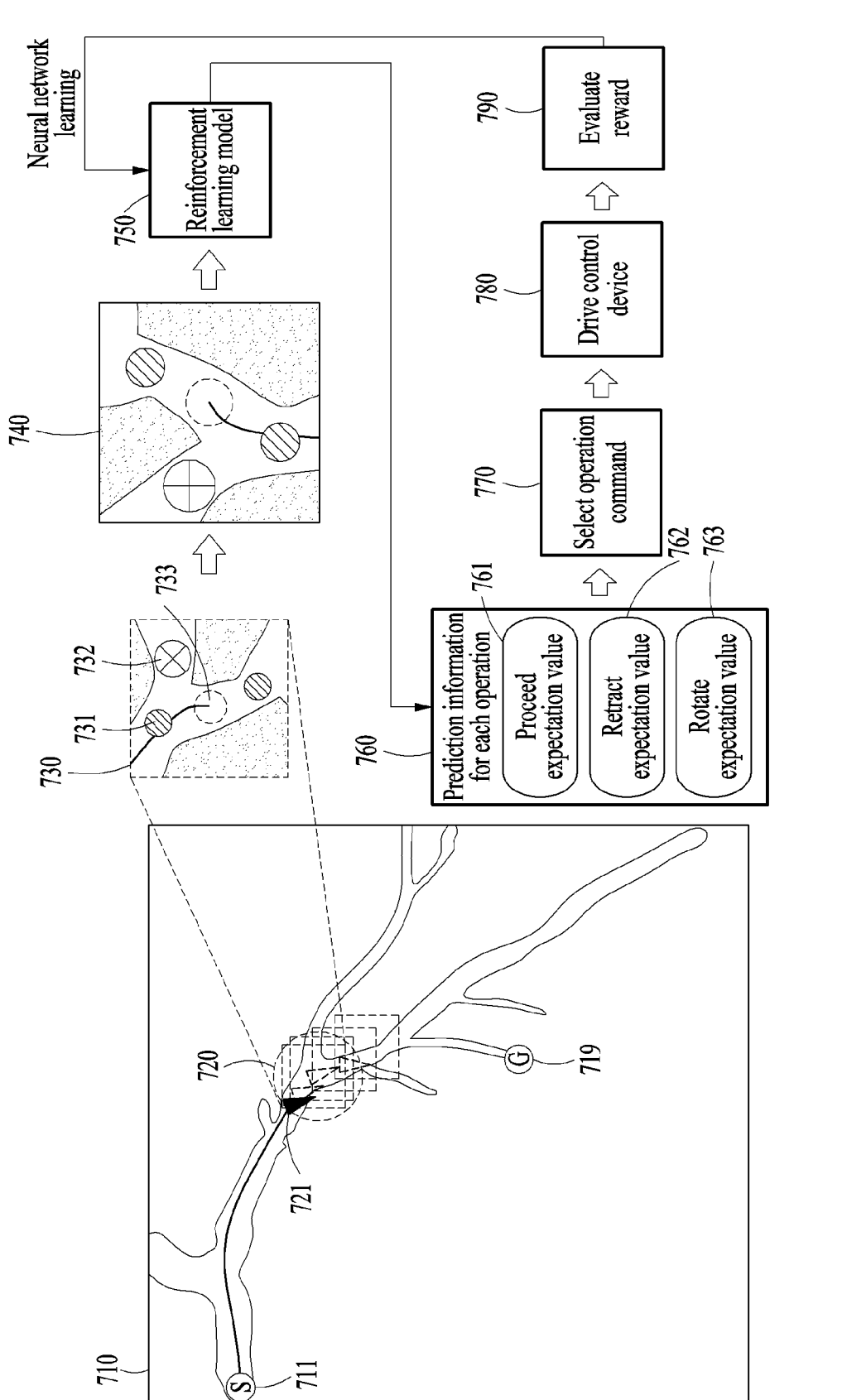
FIG. 7 is a diagram illustrating a training process of each reinforcement learning model according to an example embodiment.

FIG. 7 is a diagram illustrating a training process of each reinforcement learning model according to an example embodiment.

According to an example embodiment, the training apparatus may extract, from a vascular image 710, a vascular image patch 730 based on a location 733 of a tip 721 of a medical instrument for a branching region 720. The vascular image 710 of FIG. 7 may be an image in which a blood vessel is segmented from a CAG image. For example, the training apparatus may generate the vascular image 710 by distinguishing a vascular region from a background region by using an edge detecting method from the CAG image. For example, the edge detecting method may detect a region in which a grayscale level of an arbitrary pixel and surrounding pixels thereof rapidly changes as an edge, however the example is not limited thereto. The training apparatus may extract, from an image in which a vascular region is distinguished from a background region, a target vessel based on a thickness of a blood vessel in the vascular region and a grayscale level in the image. For example, when using angiography, a blood vessel to which a contrast medium is injected may have a lower grayscale level than a blood vessel to which a contrast medium is not injected and the thickness of a blood vessel through which a medical instrument may move may be greater than the thickness of a blood vessel through which a medical instrument may not move. Accordingly, the training apparatus may classify a blood vessel having a greater thickness than a threshold thickness and a lower grayscale level than a threshold grayscale level in a vascular region into a cardiovascular system to extract the cardiovascular system. However, the example is not limited thereto, and a different machine learning model may be used for image segmentation. In addition, although the description of image segmentation by the training apparatus is provided, a medical instrument control device may also similarly perform image segmentation for vascular region extraction.

The training apparatus may apply a reinforcement learning model 750 to the vascular image patch 730, however, in the present disclosure, an example of calculating prediction information for each operation 760 by applying the reinforcement learning model 750 to the vascular image patch 730 to which guide information is assigned is described. For example, the training apparatus may generate the guide information based on vascular structure data and the location 733 of the tip 721. However, the example is not limited thereto, and the training apparatus may receive the vascular image patch 730 to which the guide information is assigned from a vascular image capturing device. The guide information may include information indicating a destination region 719 to which the medical instrument control device and/or the training apparatus needs to move the tip of the medical instrument, a target area 731 that is in the middle of a path from a start region 711 to the destination region 719 in an image patch, and an inaccessible region 732. Information for each region may include image coordinates in a vascular image of each region, however, the example is not limited thereto. According to an example embodiment, the guide information may be render on the vascular patch image. For example, graphic objects corresponding to the target area 731, the destination region 719, and the inaccessible region 732, respectively, may be visualized by overlapping on the vascular patch image. The vascular patch image on which the guide information is visualized may be a guide patch.

The training apparatus may preprocess and align the vascular patch image 730. The training apparatus may align the vascular patch image 730 based on a proceeding direction of the medical instrument. The training apparatus may apply the reinforcement learning model 750 to an aligned image 740. Alignment of an image is described with reference to FIG. 8.

The training apparatus may calculate prediction information for each operation 760 by applying the reinforcement learning model 750 to the aligned vascular patch image 740. For example, the training apparatus may calculate the prediction information for each operation 760 by performing an operation on the aligned vascular patch image 740 based on the reinforcement learning model 750. The prediction information for each operation 760 may include a proceed expectation value 761, a retract expectation value 762, and a rotate expectation value 763. For reference, reinforcement learning may be a type of machine learning that learns three types of data, which are state, action, and reward, and in the present disclosure, the state may be an input vascular patch image and/or a guide patch, the action may be an operation command of the medical instrument control device, and the reward may be a determined value based on whether the medical instrument moves to a desired location. The expectation value may be a scalar value that shows which action is most optimal in the input state (for example, a vascular patch image to which guide information is assigned). When the reinforcement learning model 750 is optimally trained, the reinforcement learning model 750 may output the greatest expectation value for an optimal operation command among three operations.

The training apparatus may select 770 an operation command based on the prediction information for each operation 760. For example, the training apparatus may select an operation command having the greatest expectation value among expectation values calculated for a plurality of operations. The training apparatus may drive 780 a control device by the selected operation command. For example, when the proceed command is selected, the training apparatus may provide the proceed command to a driving unit of the medical instrument control device and may proceed the medical instrument.

The training apparatus may evaluate 790 a reward based on a result of applying an action to the medical instrument by driving 780 the control device. For example, the training apparatus may extract a new patch (for example, a vascular image patch) based on an updated location of the medical instrument whenever driving the medical instrument as the driving unit of the medical instrument control device performs an operation command. The training apparatus may compare an image patch corresponding to the current frame to a new image patch corresponding to a subsequent frame on which an operation command is performed. Evaluating 790 the reward is described with reference to FIG. 9.

The training apparatus may update a parameter of the reinforcement learning model 750 based on the result of evaluating 790 the reward. For example, the training apparatus may update the reinforcement learning model 750 based on evaluation data to which a reward value is applied. The evaluation data may be calculated based on a moved location of a tip of the medical instrument in an vascular image based on an operation command and may vary depending on whether a reward value is applied. The reward value may be set based on the location, time, and the number of control commands.

Before performing an operation command, the training apparatus may calculate an estimated evaluation value related to the operation command from the vascular image patch 730 corresponding to a first frame. After the tip of the medical instrument is moved based on the operation command output from the first frame, the training apparatus may calculate a measured evaluation value from a vascular image patch corresponding to a subsequent frame (for example, the second frame). The training apparatus may update a parameter of the reinforcement learning model 750 based on the estimated evaluation value and the measured evaluation value. According to an example embodiment, the training apparatus may calculate the estimated evaluation value by an expectation value calculated as the medical instrument control device performs an operation command determined by the reinforcement learning model 750 in the first frame. In addition, the training apparatus may calculate a candidate expectation value for each candidate operation command that may be performed by the medical instrument control device in the second frame and may calculate the measured evaluation value by a value obtained by adding evaluation data to the greatest candidate expectation value among the candidate operation commands. Here, the expectation value may be a cumulative reward expectation value that may be obtained as the medical instrument control device performs a series of operation commands. Accordingly, the estimated evaluation value may be a value representing a cumulative reward expectation value before the medical instrument control device performs an actual operation command. The measured evaluation value may be a value to which an obtained reward value is applied as the medical instrument control device performs an actual operation command on the greatest expectation value in a time frame after performing the actual operation command.

The training apparatus may calculate a parameter for updating the reinforcement learning model 750 based on a loss calculated by using the measured evaluation value and the estimated evaluation value. For example, the training apparatus may update the parameter of the reinforcement learning model 750 such that a difference as a loss between the measured evaluation value and the estimated evaluation value is minimized. The training apparatus may iteratively update the parameter of the reinforcement learning model 750 until the calculated loss is less than a threshold loss. In other words, the training applied may train the reinforcement learning model 750 such that the estimated evaluation value (for example, a cumulative reward expectation value estimated between the first frame and the second frame) is the same or similar to the measured evaluation value (for example, a value obtained by applying a reward value to the greatest expectation value calculated after performing the actual operation command).

In FIG. 7, the training apparatus may match an input image (for example, a vascular image patch) with an identified procedure environment in real-time during performing reinforcement learning and store the matching result in a temporary data set. Then, after reinforcement learning is finished, as described above, the training apparatus may calculate prediction information for each operation as a training output by applying the reinforcement learning model 750 to the vascular image patch stored in the temporary data set. The training apparatus may store a pair of the vascular image patch and the prediction information for each operation as training data. The training apparatus may iteratively train a plurality of reinforcement learning models by using vascular patch images collected from a plurality of branching regions of one or more vascular models.

Figure 8:
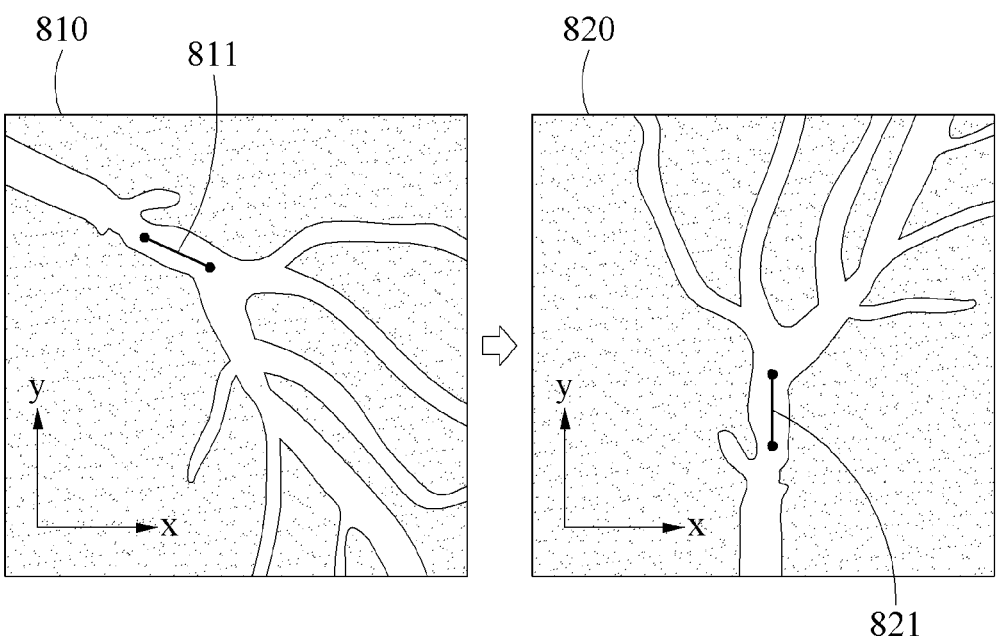
FIG. 8 is a diagram illustrating a rotation alignment of a vascular patch image according to an example embodiment.

FIG. 8 is a diagram illustrating a rotation alignment of a vascular patch image according to an example embodiment.

The training apparatus may preprocess and simplify a vascular patch image. For example, the training apparatus may simplify by performing image processing, such as smoothing, edge detecting, and the like, on a vascular region segmented from a CAG image. In addition, the training apparatus may rotate a vascular patch image such that a proceeding direction 821 of a medical instrument captured in the vascular patch image is oriented to one direction of the vascular patch image and a central axis of a branch where the medical instrument is located is aligned with an axis of the vascular patch image.

For example, the training apparatus may rotate a vascular image patch 810 based on a centerline of a branch (for example, an entry branch) where the tip of the medical instrument is located. The centerline of the branch may be a line crossing centers of portions adjacent to a branch point in the branch. The training apparatus may rotate the vascular image patch such that the centerline of the entry branch is parallel with an axis (for example, the y-axis, which is the vertical axis) of the patch. Here, the training apparatus may align the patch image such that the medical instrument is oriented to the top of the patch image. Accordingly, the training apparatus may generate a patch image 820 having consistency through rotation preprocessing to prevent recognition of a different blood vessel due to a change in an angle of a camera or an X-ray device.

Figure 9A:
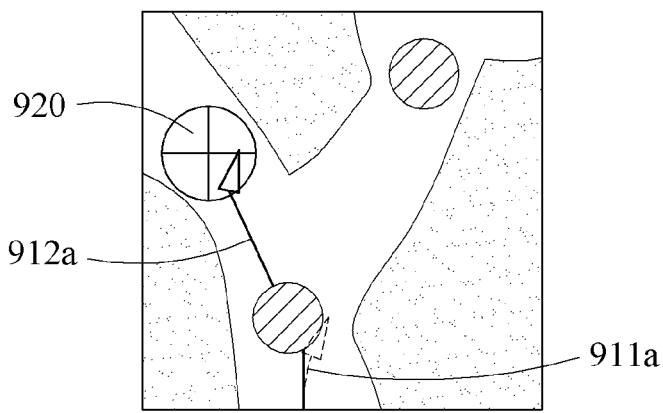
FIGS. 9A to 9C are diagrams illustrating an example of determining a compensation value of reinforcement learning according to an example embodiment.
Figure 9B:
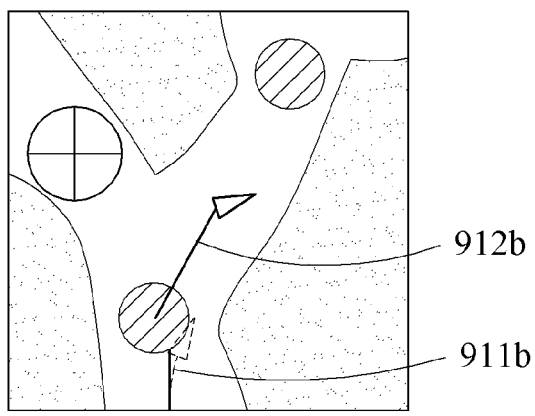
Figure 9C:
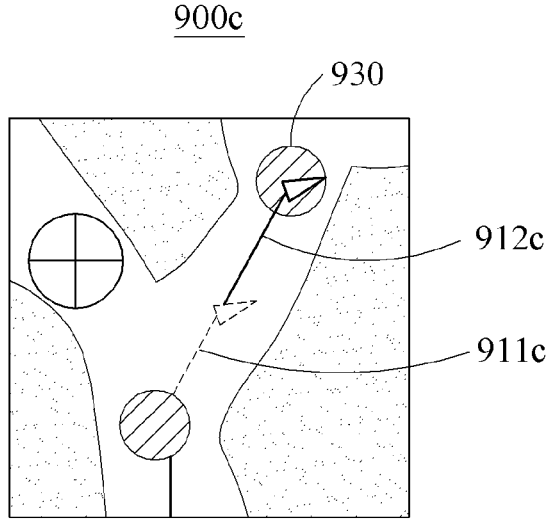

FIGS. 9A to 9C are diagrams illustrating an example of determining a compensation value of reinforcement learning according to an example embodiment.

The training apparatus may apply, to evaluation data, a reward value calculated based on a comparison result between a moved location of a tip of a medical instrument and guide information in a vascular image. The training apparatus may calculate the reward value by comparing a vascular image of a first frame to a vascular image of a second frame in which tips 911a, 911b, and 911c of a medical instrument are moved. For example, in a vascular patch image to which guide information is assigned, the training apparatus may calculate the reward value based on whether tips 912a, 912b, 912c, shown on a vascular image of the second frame, of a medical instrument respectively reach individual regions indicated by the guide information.

For example, the training apparatus may apply a first reward value to evaluation data when the tip of the medical instrument reaches a destination region. The training apparatus may apply a second reward value, less than the first reward value, to the evaluation data when the tips 911c and 912c reach an intermediate target area as shown in a patch 900c of FIG. 9C. As shown in a patch 900a of FIG. 9A, when the tip 912a reaches an inaccessible region 920, the training apparatus may apply a third reward value to the evaluation data. As shown in a patch 900b of FIG. 9B, when the tip 912b is moved to a section between regions, the training apparatus may apply a fourth reward value, wherein an absolute value of the fourth reward value is less than an absolute value of the first reward value. For reference, moving to a section between regions may represent a case where the tip of the medical instrument does not reach any one of the intermediate target area, the destination region, and the inaccessible region, but the medical instrument control device performs an operation command.

The training apparatus may generate the evaluation data by evaluating the reward as described with reference to FIGS. 9A to 9C.

Figure 10:
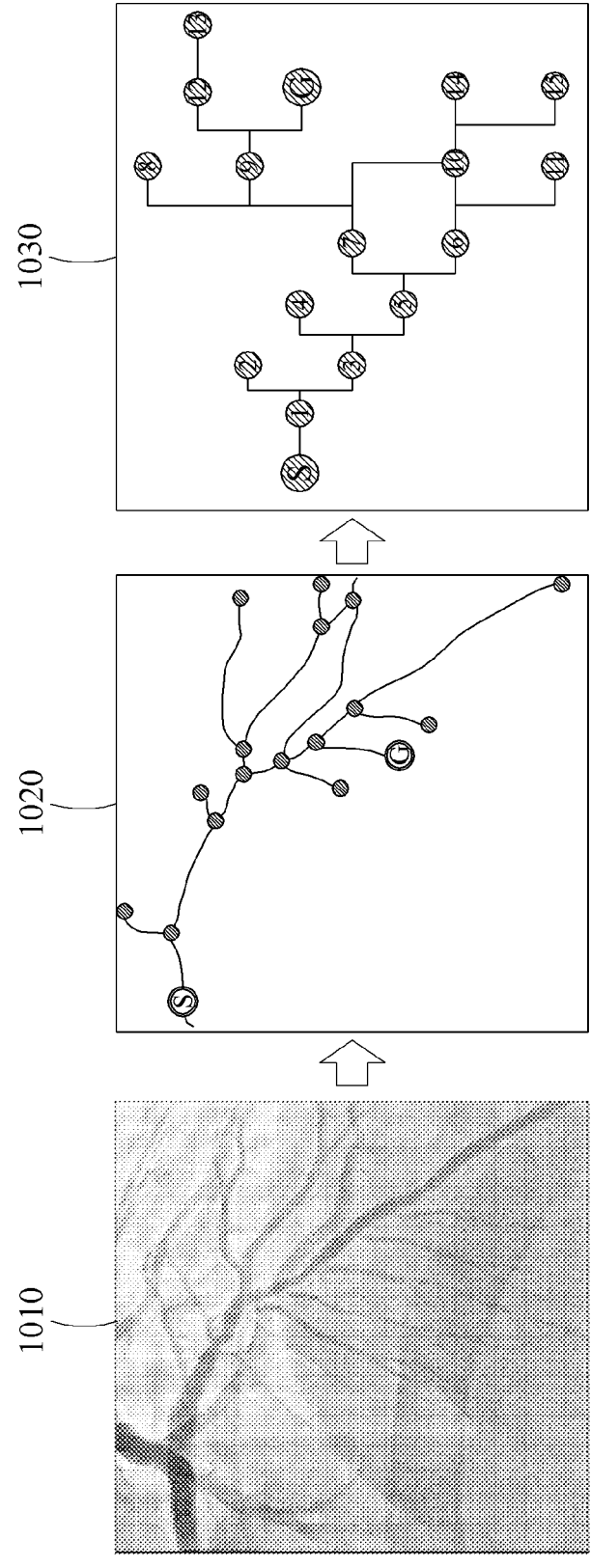
FIG. 10 is a diagram illustrating vascular structure data generated by an angiographic image according to an example embodiment.

FIG. 10 is a diagram illustrating vascular structure data generated by an angiographic image according to an example embodiment.

The training apparatus and/or the medical instrument control device may generate vascular structure data from a vascular image and may generate guide information based on the vascular structure data. For example, the training apparatus and/or the medical instrument control device may generate a vascular image 1020 by extracting and simplifying a vascular region from a CAG image 1010 and may recognize a branch and a branch point where branches intersect in the vascular image 1020. In FIG. 10, the recognized vessel branch is illustrated as a solid line and a location identified as the branching region and an endpoint of a blood vessel are illustrated as nodes.

The training apparatus and/or the medical instrument control device may generate vascular structure data 1030 based on blood vessel connection information of a branched vessel branch and an identified branching region from the vascular image 1020. The blood vessel connection information may be information representing a connection relationship between a branching region and branched blood vessels. The training apparatus and/or the medical instrument control device may generate the vascular structure data 1030 including a node indicating a branching region including a branch point and an edge indicating a vessel branch that branches off based on the branch point. The training apparatus and/or the medical instrument control device may perform data structuring on a topology of a blood vessel based on the connection information, for example, may generate a tree structure in which each node is connected to each edge wherein a branching region closest to an entry point of the blood vessel is a root node. The root node may be a node corresponding to the uppermost branch (for example, a parent blood vessel), and may be a node corresponding to a start region.

The vascular structure data 1030 may be used to generate the guide information as described above. The medical instrument control system may search the vascular structure data 1030 for a path from the root node to a node corresponding to the destination region. The medical instrument control system may select a node and an edge included in the path. The medical instrument control system may set an intermediate target area on a branch corresponding to an edge connected to a node in a branching region corresponding to the node. The medical instrument control system may set an inaccessible region on nodes and edges other than an edge to which the intermediate target area is set among edges of the vascular structure data 1030.

Figure 11:
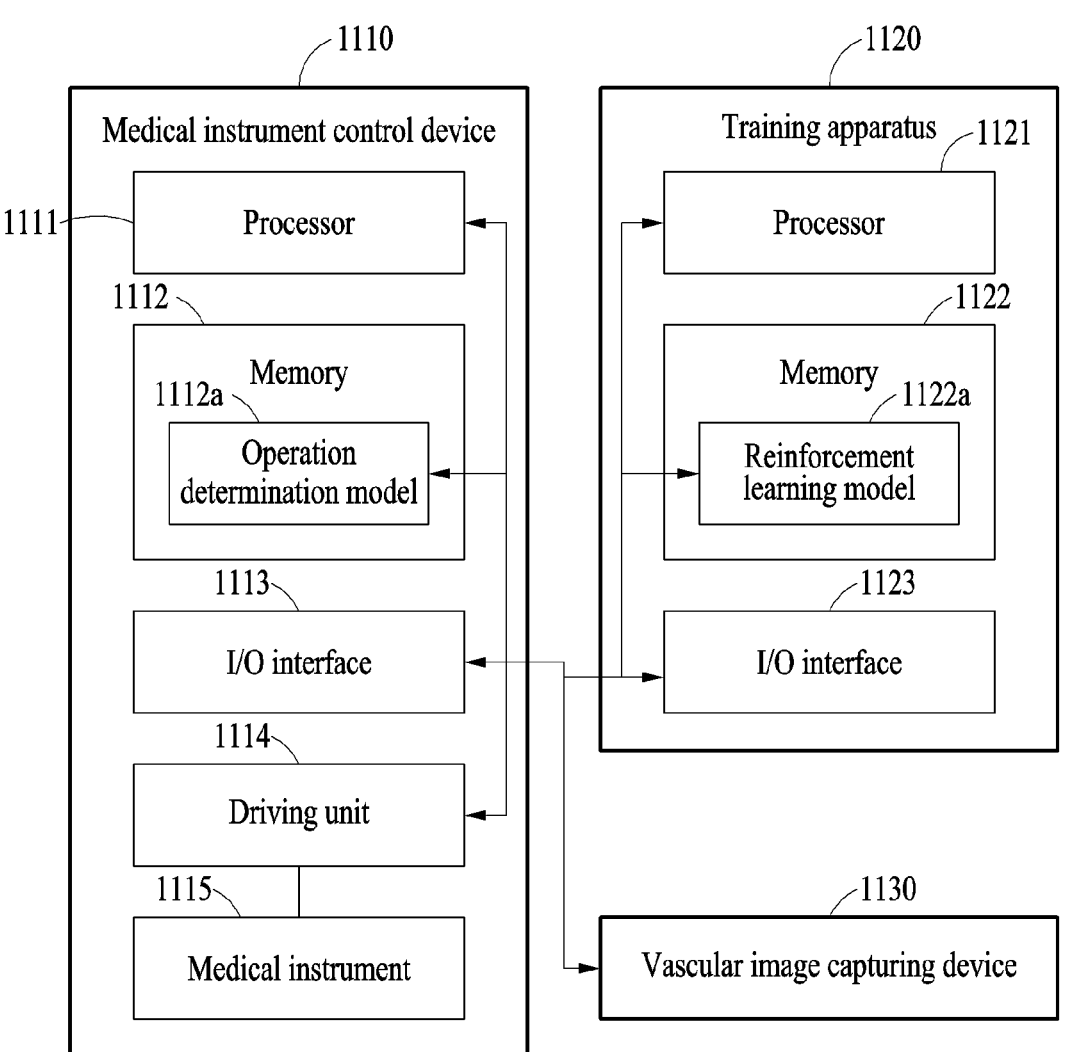
FIG. 11 is a diagram illustrating a training system of a medical instrument control device according to an example embodiment.

FIG. 11 is a diagram illustrating a training system of a medical instrument control device according to an example embodiment.

A training system 1100 of the medical instrument control device may include a medical instrument control device 1110, a training apparatus 1120, and a vascular image capturing device 1130. The vascular image capturing device 1130 may be a device for capturing an image related to a blood vessel as described with reference to FIG. 1, and thus, a detailed description thereof is omitted.

The training apparatus 1120 may include a processor 1121, a memory 1122, and an input/output (I/O) interface 1123.

The processor 1121 may train reinforcement learning models 1122a and an operation determination model 1112a. For example, the processor 1121 may identify a procedure environment of a branching region when a medical instrument 1115 inserted into a vascular model reaches the branching region in the vascular model. The processor 1121 may select a reinforcement learning model corresponding to the identified procedure environment from the plurality of reinforcement learning models. The processor 1121 may train the selected reinforcement learning model by reinforcement learning based on an extracted vascular patch image for the branching region. After training of the selected reinforcement learning model is finished, the processor 1121 may calculate a training output based on the selected reinforcement learning model from the vascular patch image for the branching region. The processor 1121 may generate training data in which as a training input, the extracted patch image pairs with the training output. The processor 1121 may train the operation determination model by supervised learning based on the generated training data. However, operations of the processor 1121 are not limited thereto, and the processor 1121 may perform operations related to training described with reference to FIGS. 1 to 10.

The memory 1122 may temporarily or permanently store data required for training. For example, the memory 1122 may store training data generated by using a vascular image, a vascular patch image, the plurality of reinforcement learning models 1122a, and reinforcement learning models 1122a. In addition, FIG. 11 illustrates an example that the operation determination model 1112a is stored in the memory 1112 of the medical instrument control device 1110, however, while the operation determination model 1112a is trained, the memory 1122 of the training apparatus 1120 may store the operation determination model 1112a. The training apparatus 1120 may store the operation determination model 1112a during training and when training is finished, may transmit the operation determination model 1112a to the medical instrument control device 1110 via the I/O interface 1123.

The I/O interface 1123 may be a data interface configured to transmit/receive data required for training the reinforcement learning models 1122a and the operation determination models 1112a. For example, the I/O interface 1123 may receive an image related to a blood vessel from the vascular image capturing device 1130. In addition, the I/O interface 1123 may output a command to control a driving unit 1114 to the medical instrument control device 1110 during reinforcement learning.

The medical instrument control device 1110 may include a processor 1111, a memory 1112, an I/O interface 1113, the driving unit 1114, and a medical instrument 1115. The driving unit 1114 may be a module configured to drive the medical instrument 1115 in response to a determined operation command, the medical instrument 1115 may be a member connected to the driving unit 1114 through a medical wire, and since the description thereof is provided above, the detailed description is omitted.

During training (for example, reinforcement learning), the processor 1111 may receive an operation command from the training apparatus 1120 and may control the driving unit 1114.

After training is finished, the processor 1111 may control the medical instrument 1115 by using the operation determination model 1112a stored in the memory 1112. For example, when the medical instrument 1115 is inserted into a blood vessel for vascular intervention, the processor 1111 may receive a vascular image that captures a body blood vessel of a recipient from the vascular image capturing device 1130 via the I/O interface 1113. The processor 1111 may extract a vascular patch image based on a location of the medical instrument 1115 from the vascular image and may calculate prediction information for each operation based on the operation determination model 1112a from the extracted vascular patch image. Unlike training, while the medical instrument 1115 is inserted, the processor 1111 of the medical instrument control device 1110 may calculate an expectation value for each operation command as an output by using the operation determination model from an extracted input patch image based on a location of the medical instrument 1115 inserted into a blood vessel without procedure environment information. The operation determination model 1112a, which is a student trained by reinforcement learning models 1122a for each procedure environment, which is a teacher, may be trained to output an optimal expectation value for various procedure environments. The processor 1111 may select an operation command having the greatest expectation value among the calculated expectation values for each operation command. The processor 1111 may perform any one of proceeding, rotating, and retracting on the medical instrument 1115 by driving a driving unit connected to the medical instrument 1115 based on the selected operation command.

The training system 1100 of the medical instrument control device may collect training data for variously defined procedure environments and may train the operation determination model 1112a, which is a single integrated neural network, by using the collected training data for different vascular models at different times. The trained operation determination model 1112a may have a high success rate of moving the medical instrument 1115 to a target area and a destination region in a blood vessel in various environments.

The training system 1100 of the medical instrument control device may integrate reinforcement learning models 1122a overfitted for various procedure environments into the single operation determination model 1112a through supervised learning. As described above, the operation determination model 1112a may show a high success rate not only for an environment used for training as a generalized model for various environments but also for an environment that is not used for training.

The methods according to the above-described examples may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter. The above-described devices may be configured to act as one or more software modules in order to perform the operations of the above-described example embodiments, or vice versa.

The software may include a computer program, a piece of code, an instruction, or some combination thereof, to independently or uniformly instruct or configure the processing device to operate as desired. Software and data may be embodied permanently or temporarily in any type of machine, component, physical or pseudo equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A method, performed by a processor, of training an operation determination model of a medical instrument control device, the method comprising:

when a medical instrument inserted into a vascular model reaches a branching region in the vascular model, identifying a procedure environment in the branching region;

selecting a reinforcement learning model corresponding to the identified procedure environment from a plurality of reinforcement learning models and training the selected reinforcement learning model by reinforcement learning based on a vascular patch image extracted for the branching region;

after training of the selected reinforcement learning model is finished, calculating a training output based on the selected reinforcement learning model from the vascular patch image for the branching region and generating training data in which the training output pairs with the extracted vascular patch image as a training input; and training the operation determination model by supervised learning based on the generated training data.

2. The method of claim 1, wherein the identifying of the procedure environment comprises when the medical instrument reaches the branching region, identifying a branching shape of the branching region based on the vascular patch image extracted for the branching region.

3. The method of claim 2, wherein the identifying of the branching shape comprises identifying based on an angle difference between a direction of a main branch and a direction of branch closest to a branch point in the vascular patch image.

4. The method of claim 1, wherein the identifying of the procedure environment comprises when the medical instrument reaches the branching region, identifying an orientation characteristic of a tip of the medical instrument in the branching region.

5. The method of claim 4, wherein the identifying of the orientation characteristic comprises:

when the medical instrument rotates in a predetermined rotation angle based on a longitudinal direction axis of a medical wire connected to a body of the medical instrument, observing an orientation direction of the tip of the medical instrument; and calculating a ratio of observed directions during rotation of the medical instrument and determining the orientation characteristic based on the calculated ratio.

6. The method of claim 1, wherein the identifying of the procedure environment comprises when a plurality of vascular patch images for the branching region is extracted, mapping a procedure environment, which is identified for one vascular patch image from among the plurality of vascular patch images, to the other vascular patch images.

7. The method of claim 6, wherein the identifying of the procedure environment comprises until the medical instrument enters the branching region and reaches an outside of the branching region, extracting a plurality of vascular patch images related to the branching region based on a location of the medical instrument that changes each time the medical instrument drives, wherein the training of the selected reinforcement learning model by reinforcement learning comprises training the selected reinforcement learning model corresponding to the identified procedure environment, based on the plurality of vascular patch images related to the branching region.

8. The method of claim 1, further comprising:

preprocessing and simplifying the vascular patch image.

9. The method of claim 8, wherein the simplifying comprises rotating the vascular patch image such that a proceeding direction of the medical instrument captured in the vascular patch image is oriented to one direction of the vascular patch image and a central axis of a branch where the medical instrument is located is aligned with an axis of the vascular patch image.

10. The method of claim 1, wherein the training of the selected reinforcement learning model by reinforcement learning comprises when a reinforcement learning model corresponding to the identified procedure environment for the branching region is not found, excluding at least a portion of vascular patch images related to the branching region from training.

11. The method of claim 10, wherein the excluding comprises excluding, from training based on reinforcement learning, vascular patch images related to a branching region having a branching shape with an angle difference that is out of a predetermined angular range designated to a plurality of reinforcement learning models.

12. The method of claim 1, wherein the training of the selected reinforcement learning model by reinforcement learning comprises iteratively training the plurality of reinforcement learning models by using vascular patch images collected from a plurality of branching regions of one or more vascular models.

13. The method of claim 1, wherein the identifying of the procedure environment comprises mapping the identified procedure environment to the vascular patch image, wherein the generating of the training data comprises:

for each of the plurality of vascular patch images collected during training of the plurality of reinforcement learning models, loading a reinforcement learning model corresponding to the procedure environment that is mapped to the vascular patch image; and generating the training output by applying the loaded reinforcement learning model to the vascular patch image.

14. The method of claim 1, wherein the training of the operation determination model comprises updating a parameter of the operation determination model until a loss between the training output and an output calculated based on the operation determination model from the vascular patch image is less than a threshold loss.

15. The method of claim 1, further comprising:

while the medical instrument is inserted, calculating an expectation value for each operation command as an output by using the operation determination model from an input patch image that is extracted based on a location of the medical instrument inserted into a blood vessel without procedure environment information.

16. The method of claim 15, further comprising:

selecting an operation command having a greatest expectation value among expectation values calculated for each operation command; and performing any one of proceeding, rotating, and retracting of the medical instrument by driving a driving unit connected to the medical instrument based on the selected operation command.

17. A non-transitory computer-readable storage medium storing instructions that, when executed by a processor, cause the processor to perform a method comprising the steps of:

when a medical instrument inserted into a vascular model reaches a branching region in the vascular model, identifying a procedure environment in the branching region;

selecting a reinforcement learning model corresponding to the identified procedure environment from a plurality of reinforcement learning models and training the selected reinforcement learning model by reinforcement learning based on a vascular patch image extracted for the branching region;

after training of the selected reinforcement learning model is finished, calculating a training output based on the selected reinforcement learning model from the vascular patch image for the branching region and generating training data in which the training output pairs with the extracted vascular patch image as a training input; and training the operation determination model by supervised learning based on the generated training data.

18. A system for training an operation determination model of a medical instrument control device, the system comprising:

a memory configured to store a plurality of reinforcement learning models and operation determination models; and a processor configured to, when a medical instrument inserted into a vascular model reaches a branching region in the vascular model, identify a procedure environment in the branching region, select a reinforcement learning model corresponding to the identified procedure environment among the plurality of reinforcement learning models, train the selected reinforcement learning model by reinforcement learning based on a vascular patch image extracted for the branching region, after training of the selected reinforcement learning model is finished, calculate a training output based on the selected reinforcement learning model from the vascular patch image for the branching region, generate training data in which the training output pairs with the extracted vascular patch image as a training input, and train the operation determination model by supervised learning based on the generated training data.

* * * * *